United States Patent
Williams et al.

(10) Patent No.: US 6,803,579 B2
(45) Date of Patent: Oct. 12, 2004

(54) TECHNIQUE FOR REMOVAL OF PICKET FENCE EFFECT IN PET IMAGING SYSTEMS

(75) Inventors: John Jay Williams, Hartland, WI (US); David Leo McDaniel, Dousman, WI (US)

(73) Assignee: General Electric Company, Schenectady, NY (US)

( * ) Notice: Subject to any disclaimer, the term of this patent is extended or adjusted under 35 U.S.C. 154(b) by 412 days.

(21) Appl. No.: 09/966,857

(22) Filed: Sep. 28, 2001

(65) Prior Publication Data

US 2003/0062482 A1 Apr. 3, 2003

(51) Int. Cl.$^7$ ................................................ G01T 1/164

(52) U.S. Cl. ................................... 250/363.03; 702/189

(58) Field of Search ...................... 250/363.03; 702/189

(56) References Cited

U.S. PATENT DOCUMENTS 5,241,181 A * 8/1993 Mertens et al. ........ 250/363.03

\* cited by examiner

*Primary Examiner*—Constantine Hannaher
*Assistant Examiner*—Shun Lee
(74) *Attorney, Agent, or Firm*—Quarles & Brady LLP; Carl B. Horton

(57) ABSTRACT

A method and apparatus for eliminating the picket fence effect in PET scanners where the scanner includes a master clock and an event processing circuit that generates time stamps during each clock cycle, the scanner also including a coincidence detector that compares the time stamps during each clock cycle to identify coincidence events, the method including the steps of, for consecutive master clock cycles, identifying an overlap period that includes a portion of a first of the master cycles adjacent a second of the master cycles, adding an overlap period that occurs during the overlap period to the second of the master cycles to generate an extended cycle, identifying overlap events that occur during the overlap period in the first of the master cycles, copying the overlap events to the overlap period in the extended second cycle and performing a comparison of the events in the extended cycle to identify coincidence event pairs

20 Claims, 5 Drawing Sheets

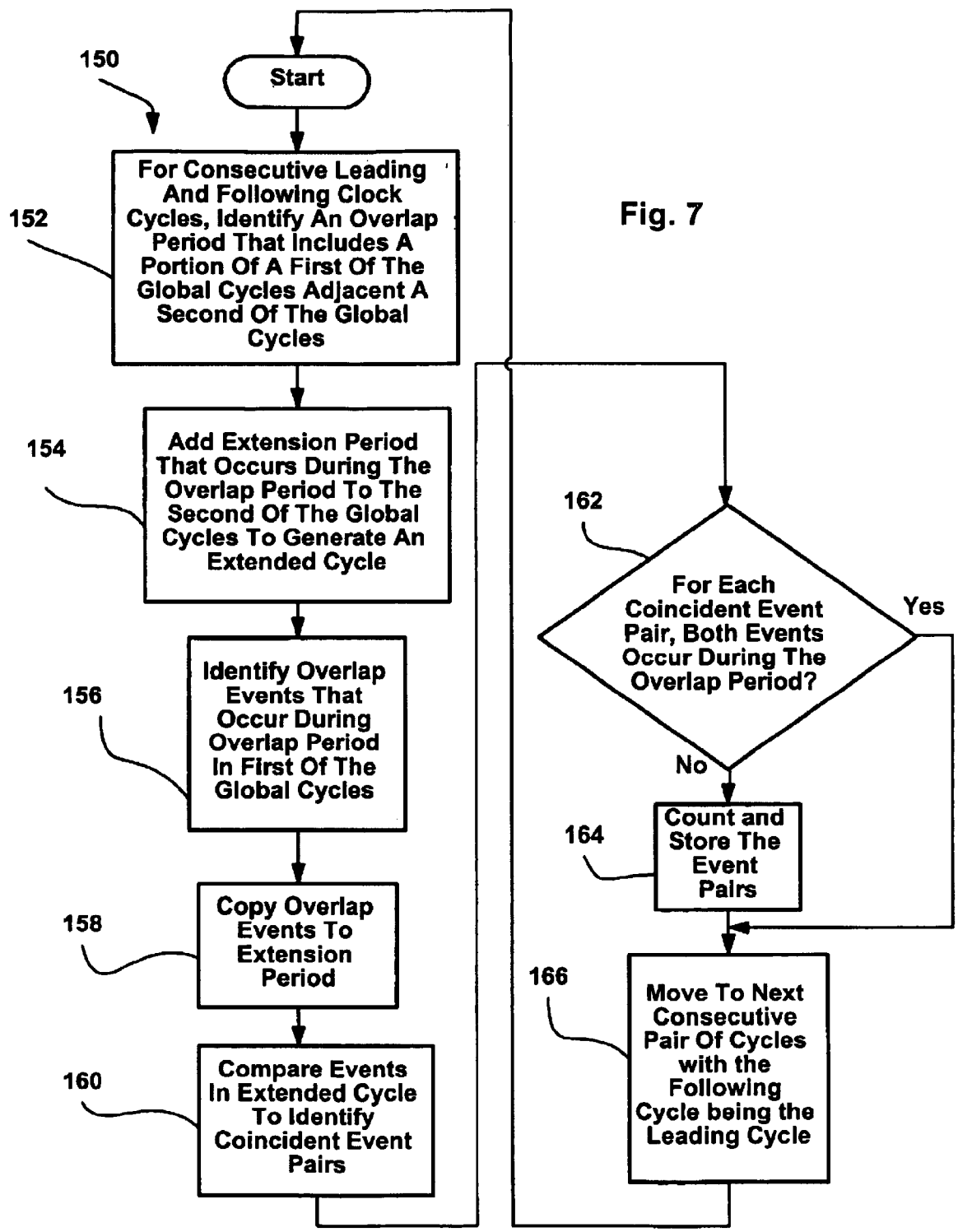

TECHNIQUE FOR REMOVAL OF PICKET FENCE EFFECT IN PET IMAGING SYSTEMS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to PET scanners generally and specifically to a method and apparatus for increasing the counting efficiency of a digital time stamping PET scanner by eliminating counting error due to the "picket fence" effect.

Positrons are positively charged electrons which are emitted by radionuclides which have been prepared using a cyclotron or other device. The radionuclides most often employed in diagnostic imaging are fluorine-18, carbon-11, nitrogen-13 and oxygen-15. Radionuclides are employed as radioactive tracers called "radiopharmaceuticals" by incorporating them into substances such as glucose or carbon dioxide. One common use for radiopharmaceuticals is in the medical imaging field.

To use a radiopharmaceutical in imaging, the radiopharmaceutical is injected into a patient and accumulates in an organ, vessel or the like, which is to be imaged. It is known that specific radiopharmaceuticals become concentrated within certain organs or, in the case of a vessel, that specific radiopharmeceuticals will not be absorbed by a vessel wall. The process of concentrating often involves processes such as glucose metabolism, fatty acid metabolism and protein synthesis. Hereinafter, in the interest of simplifying this explanation, an organ to be imaged will be referred to generally as an "organ of interest" and prior art and the invention will be described with respect to a hypothetical organ of interest. After a radiopharmaceutical becomes concentrated within an organ of interest and while the radionuclides decay, the radionuclides emit positrons. The positrons travel a very short distance before they encounter an electron and, when the positron encounters an electron, the positron is annihilated and converted into two photons, or gamma rays. This annihilation event is characterized by two features which are pertinent to medical imaging and particularly to medical imaging using photon emission tomography (PET). First, each gamma ray has an energy of essentially 511 keV upon annihilation. Second, the two gamma rays are directed in substantially opposite directions.

In PET imaging, if the general locations of annihilations can be identified in three dimensions, the shape of an organ of interest can be reconstructed for observation. To detect annihilation locations, a PET scanner is employed. An exemplary PET scanner includes a plurality of detector modules and a processor which, among other things, includes coincidence detection circuitry. An exemplary detector module includes six adjacent detector units. An exemplary detector unit includes an array of crystals (e.g. 36) and a plurality of photo-multiplier tubes (PMTs). The crystal array is located adjacent to the PMT detecting surfaces. When a photon impacts a crystal, the crystal generates light which is detected by the PMTs. The PMT signal intensities are combined and the combined signal is compared to a threshold energy level (e.g. 100 keV). When the combined signal is above the threshold, an event detection pulse (EDP) is generated which is provided to the processor coincidence circuitry. Other hardware determines which crystal generated the light (i.e. absorbed the photon).

The coincidence circuitry identifies essentially simultaneous EDP pairs which correspond to crystals which are generally on opposite sides of the imaging area. Thus, simultaneous pulse pair indicates that an annihilation has occurred on a straight line between an associated pair of crystals. Over an acquisition period of a few minutes, millions of annihilations are recorded, each annihilation associated with a unique crystal pair. After an acquisition period, recorded annihilation data is used via any of several different well known procedures to construct a three dimensional image of the organ of interest.

A PET scanner may test the energy level before or after testing for coincidence timing and the coincidence timing test may be either analog or digital. In a typical analog coincidence circuit the duration of a timing signal is set to a pre-determined value (e.g. W/2 where W is a time period corresponding to a coincidence window). The timing signals from the detector units are then combined using conventional AND logic gate which produces an output only when two timing pulses overlap (i.e. two consecutive pulses are within +/−W/2).

In a typical digital coincidence circuit each EDP timing signal is compared to a master clock signal in a time to digital converter (TDC) and a time stamp digital value is provided for the EDP. The time stamp digital value from the TDC corresponds to the time lapsed between the previous master clock pulse and the EDP. For instance, in one exemplary system a master clock cycle may be 250 nanoseconds and the TDC may be capable of further dividing each master cycle into 192 separate sub-periods. For the purposes of this explanation a master clock cycle of 250 nanoseconds and further division of each cycle into 192 time stamps will be assumed although other cycle divisions and stamp divisions are completed. After each master clock cycle the time stamps corresponding to all EDPs detected during the completed master clock cycle (i.e. the stamps which occurred between the preceding two master clock pulses) are compared. EDPs which have time stamp differences between the time stamps of smaller than +/−W/2 are identified as coincidence pairs.

During an acquisition period there are several sources of annihilation detection error. One source of error in systems that include digital coincidence circuitry is referred to as the "picket fence effect". To this end, as indicated above, event detection pulses are generated relative to a master clock cycle and thereafter all time stamps corresponding to pulses that occurred during the master clock cycle are compared to identify coincidence pairs. In this type of system, EDPs that occur either near the beginning or the end of a master clock cycle may have a matching coincidence event that falls into either a previous or a subsequent master clock cycle. Coincidence pairs including EDPs that "straddle" two master clock cycles are effectively lost as the coincidence circuitry has no way to associate the two EDPs with a single annihilation event. In some cases event losses due to the picket fence effect have accounted for as much as 1% of the total possible signal. The amount of loss depends on the width of the event time stamp and period of the master clock cycle. In the case of wide time stamp and short clock cycle, this loss can be several percent.

The picket fence phenomenon can best be understood by example and, to this end, refer to FIG. 4 where a timing diagram 98 illustrates the end and the beginning of consecutive leading and following master clock cycles, respectively, along with exemplary EDPs. The end of the leading cycle as illustrated includes time stamps 186 through 191 while the beginning of the following cycle includes time stamps 0 through 5. The EDPs that have time stamps during the leading cycle are identified by downwardly directed arrows while the EDPs that have time stamps during the following cycle are identified by upwardly directed arrows. Six exemplary EDPs 11, 21, 31, 41, 51 and 61 are illustrated with EDPs 11, 21 and 31 occurring during the leading clock cycle and having time stamps 186, 188 and 190, respectively, while EDPs 41, 51 and 61 occur during the following clock cycle and having time stamps 0, 2 and 5.

For this example, assume that the EDPs 11, 21, 31, 41, 51 and 61 correspond to three separate annihilation events. In addition, assume a coincidence window W period corresponding to 12 consecutive time stamps. In this case, half the coincidence window (i.e., W/2) corresponds to six time stamp periods and therefore, any two EDPs having time stamps within 6 time stamp periods of each other should be considered for coincidence pairing.

Thus, referring still to FIG. 4, while EDPs 11, 21, 31, 41, 51 and 61 correspond to three separate annihilation events, potential coincidence pairs may include EDPs 11 and 21 (i.e., EDPs 11 and 21 may correspond to a single event), EDPs 21 and 31, EDPs 31 and 41, EDPs 41 and 51, EDPs 51 and 61, EDPs 11 and 31, EDPs 11 and 41, EDPs 21 and 41, EDPs 21 and 51, EDPs 31 and 41, EDPs 31 and 51 and EDPs 41 and 61. Nevertheless, exemplary coincidence detection circuitry would fail to recognize many of the potential coincidence pairings because the circuitry would not compare EDP time stamps between the leading and following cycles. Specifically, in this example, in the leading cycle, the coincidence circuitry would consider pairing EDPs 11 and 21, 21 and 31 and 11 and 31, while in the following cycle the circuitry would consider pairing EDPs 41 and 51, 41 and 61 and 51 and 61. The circuitry would ignore possible EDP pairings 21 and 41, 21 and 51, 31 and 41, and 31 and 51. Thus, assuming that, based on other signal characteristics (e.g., angles between crystals that generate EDPs, etc.), the coincidence circuitry identifies coincidence pairs including EDPs 11 and EDPs 21 and 51 and 61 ("found and accepted" pairs as illustrated), the circuitry would miss the potential pair including EDPs 31 and 41 ("missed, no match" as illustrated).

One way to eliminate this dual clock period loss of events is to acquire data in a list mode during acquisition, store the acquired data and subsequently process the data to identify coincidence events. This solution, while ideal, is impractical with existing systems as the computational and archiving overhead would be excessive.

Another way to avoid picket fence related loss of events would be to repeat the coincidence comparison for clock cycles that are shifted so that they include the time stamps at both the end of one "normal" cycle and the beginning of another cycle. In this case, coincidence pairs having EDPs in consecutive normal clock cycles would be detected and counted. While theoretically feasible, this solution, unfortunately, would require a second complete comparison circuit which would be far too expensive for most applications.

Faced with the aforementioned problems and the realization that picket fence related losses are relatively minimal (e.g., 1% of the total possible signal level), the industry has generally accepted picket fence effect losses. Nevertheless, as other system parameters and performance have been improved, newer systems have adopted or will be adopting master clocks that have shorter master clock cycles. Because the picket fence effect loss occurs at the end of every master clock cycle, the picket fence related error is inversely proportional to the master clock period such that shorter clock cycles cause greater error (e.g., an error >1% of the total signal). Thus, the picket fence effect error will be increasing and, at least for some applications, may be at unacceptable levels.

BRIEF SUMMARY OF THE INVENTION

An exemplary embodiment of the invention includes a method for reducing event loss in a digital time stamped PET scanner including a master clock that has a master clock cycle and an event processing circuit that divides each clock cycle into a plurality of time stamps. The scanner also including coincidence detection circuitry that compares time stamps within each clock cycle to identify coincidence event pairs. The method comprises the steps of, for consecutive leading and following clock cycles where each of the leading and following cycles are master cycles, identifying an overlap period that includes a portion of a first of the master cycles adjacent a second of the master cycles, adding the overlap period to the second of the master cycles to generate an extended cycle, identifying overlap events that occur during the overlap period in the first of the master cycles, copying the overlap events to the overlap period in the extended cycle, comparing events in the extended cycle to identify coincidence event pairs and counting the event pairs.

In at least some embodiments the step of comparing includes, for each coincidence event pair, determining if both events in the pair occur during the overlap period and, where both events occur during the overlap period, skipping the step of counting the event pair. In some embodiments the leading cycle and following cycle are the first and second cycles, respectively, so that the step of identifying an overlap period includes the step of identifying the ending portion of the leading cycle adjacent the following cycle. In other embodiments the leading cycle and following cycle are the second and first cycles, respectively, so that the step of identifying an overlap period includes the step of identifying the beginning portion of the following cycle adjacent the leading cycle.

In some embodiments the scanner is characterized by a coincidence window and the overlap period has a duration at least as long as one half the coincidence window.

In addition to the method, the invention includes other similar methods and also contemplates an apparatus that includes either dedicated hardware or that may be implemented in software as computer programs that represent algorithms for execution by a conventional-type digital processor adapted for imaging applications.

These and other aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

BRIEF DESCRIPTION OF THE SEVERAL VIEWS OF THE DRAWINGS

FIG. 7 is a flow chart illustrating an exemplary method to the present invention.

DETAILED DESCRIPTION OF THE INVENTION

Figure 1:
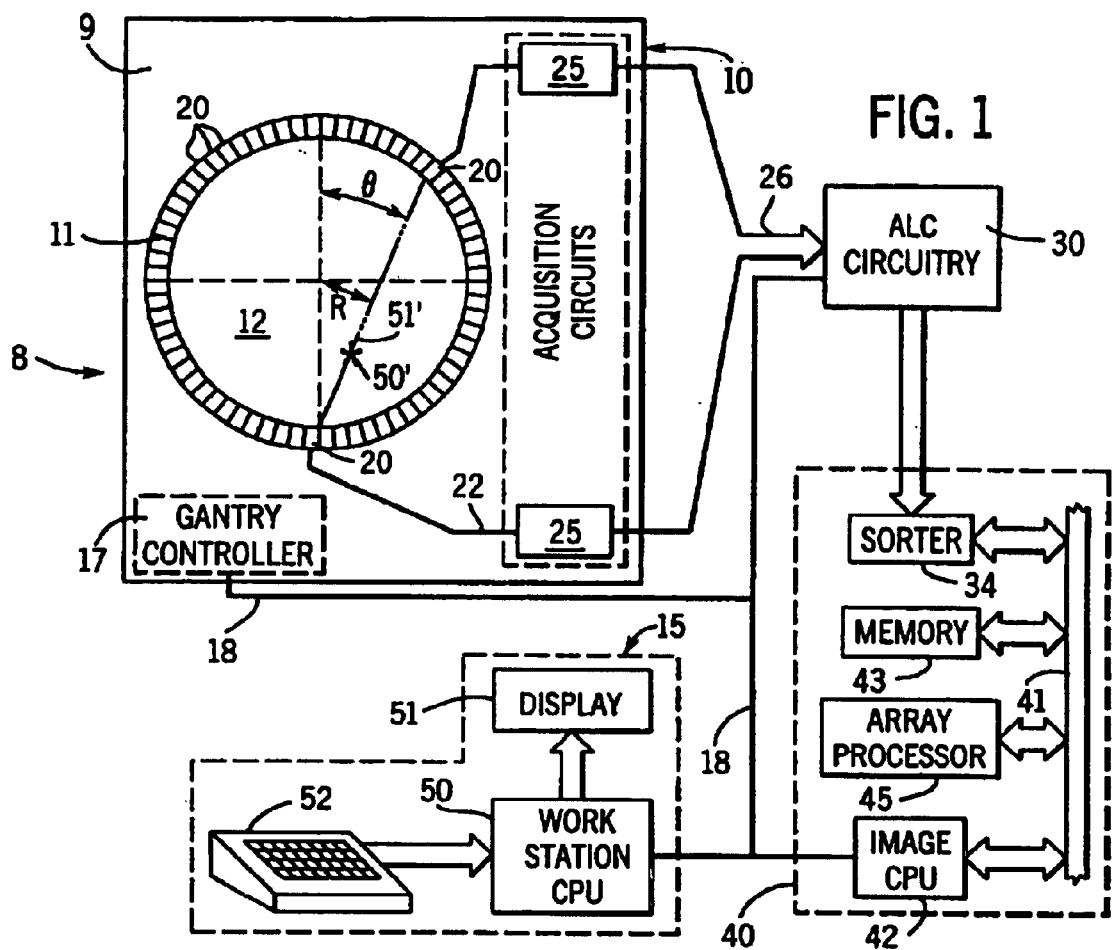
FIG. 1 is a schematic view of a PET system for implementing the present invention.

Referring now to the drawings wherein like reference characters and symbols represent corresponding elements and signals throughout the several views and, more specifically, referring to FIG. 1, the present invention will be described in the context of an exemplary PET scanner system 8. System 8 includes an acquisition system 10, an operator work station 15, acquisition, locator and coincidence (ALC) circuitry 30 and an image reconstruction processor 40.

System 10 includes a gantry 9 which supports a detector ring assembly 11 about a central bore which defines an imaging area 12. A patient table (not illustrated) is positioned in front of gantry 9 and is aligned with imaging area 12. A patient table controller (not shown) moves a table bed into imaging area 12 in response to commands received from work station 15 through a serial communications link 18.

A gantry controller 17 is mounted within gantry 9 and is responsive to commands received from operator work station 15 through link 18 to operate gantry 9. For example, gantry 9, can perform a "coincidence timing calibration scan" to acquire corrective data, or can perform a normal "emission scan" in which positron annihilation events are counted.

Figure 2:
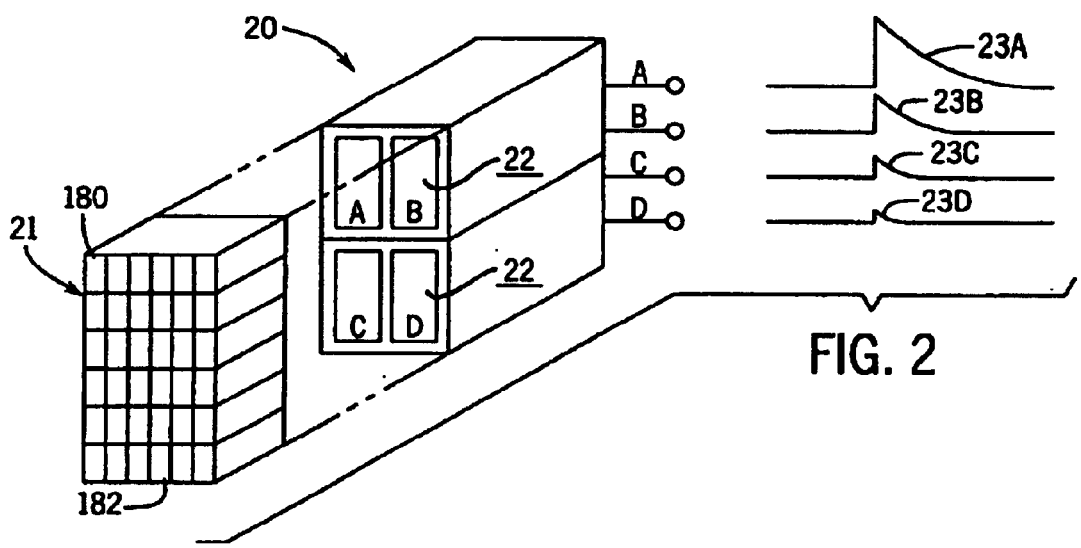
FIG. 2 is a perspective view of a detector unit and associated PMT signals.

As shown best in FIG. 2, assembly 11 is comprised of a large number of detector units 20. Although not illustrated, detector units 20 are arranged in modules, each module including six separate and adjacent detector units 20. A typical assembly 11 includes 56 separate modules such that each assembly 11 includes 336 separate detector units 20. Each unit 20 includes a set of bismuth germinate (BGO) scintillator crystals 21 (two separate crystals identified by numerals 180 and 182) arranged in a 6×6 matrix and disposed in front of four photo multiplier tubes (PMTs) A, B, C and D which are collectively referred to by numeral 22. When a photon impacts a crystal 21, a scintillation event occurs and the crystal generates light which is directed at PMTs 22. Each PMT 22 receives at least some light generated by the scintillation event and produces an analog signal 23A–23D which arises sharply when a scintillation event occurs and then tails off exponentially with a time constant of approximately 300 nanoseconds. The relative magnitudes of the analog signals 23A–23D are determined by the position in the 6×6 BGO matrix at which a scintillation event takes place, and the total magnitude of these signals is determined by the energy of a photon which causes the event.

Referring still to FIGS. 1 and 2, a set of acquisition circuitry 25 is mounted within gantry 9 to receive the four signals 23A–23D from each detector unit 20 in assembly 11. Circuitry 25 provides signals 23A–23D to ALC circuitry 30 via a data bus 26. Circuitry 30 uses the signals 23A–23D to determine the energy of a detected event, if the energy detected likely corresponds to a photon, the actual coordinates of a detected event within the block of BGO crystals 21, the time of the event (i.e. generates a time stamp) and compares event times to identify coincidence pairs of events that are stored as coincidence data packets. Each coincidence data packet includes a pair of digital numbers which precisely identify the addresses of the two BGO crystals 21 that detected an associated event. Operation of ALC circuitry 30 is explained more in detail below.

Referring again to FIG. 1, processor 40 includes a sorter 34, a memory module 43, an array processor 45, an image CPU 42 and a backplane bus 41 which conforms to the VME standards and links all other processor components together. The primary purpose of sorter 34 is to generate memory addresses for the coincidence data packets to efficiently store coincidence data. The set of all projection rays that point in the same direction and pass through the scanner's FOV is a complete projection, or "view". A distance R between a particular projection ray and a center of the FOV locates that projection ray within the FOV. As shown in FIG. 1, for example, a positron annihilation (hereinafter an "event") 50' occurs along a projection ray 51' which is located in a view at the projection angle θ and the distance R. The sorter 34 counts all of the events which occur on this projection ray (R, θ) during an acquisition period by sorting out the coincidence data packets that indicate an event at the two BGO detector crystals lying on ray 51'.

During a data acquisition, the coincidence counts are organized in memory 43 as a set of two-dimensional arrays, one for each axial image, and each having as one of its dimensions the projection angle θ and the other dimension the distance R. This θ by R map of detected events is called a histogram. Coincidence events occur at random and sorter 34 quickly determines the θ and R values from the two crystal addresses in each coincidence data packet and increments the count of the corresponding sinogram array element. At the completion of an acquisition period, memory 43 stores the total number of annihilation events which occurred along each ray (R, θ) in the histogram.

Image CPU 42 controls bus 41 and links processor 40 to local network 18. Array processor 45 also connects to the bus 41 and operates under the direction of image CPU 42 to facilitate image reconstruction using histogram data from memory module 43. The resulting image array is stored in memory module 43 and is output by image CPU 42 to operator work station 15.

Station 15 includes a CPU 50, a CRT display 51 and a keyboard 52. CPU 50 connects to network 18 and scans key board 52 for input information. Through the keyboard 52 and associated control panel switches, an operator can control calibration of system 9, its configuration, and the positioning of a patient table (not illustrated during data acquisition.

Figure 3:
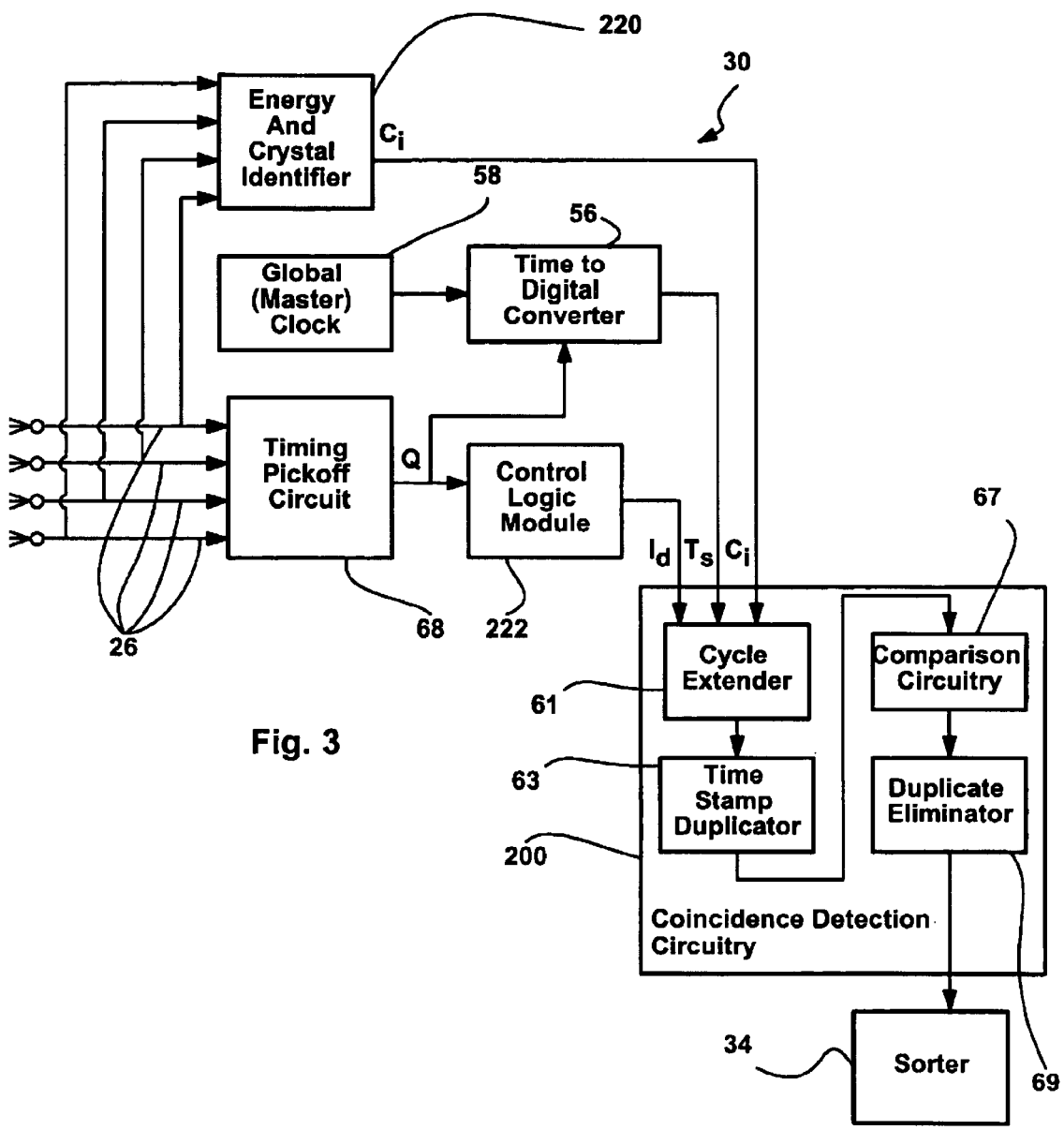
FIG. 3 is a schematic view of the ALC circuitry of FIG. 1.

Referring to FIGS. 1, 2 and 3, for each separate detector module (i.e. grouping of six detector units 20) within an assembly 11, ALC circuitry 30 includes the hardware illustrated in FIG. 3. For each separate detector unit 20 within a module the hardware includes an energy and crystal identifier 220, a master clock 58, a time to digital converter (TDC) 56, coincidence detection circuitry 200, a timing pick-off circuit (TPC) 68 and a control logic module 222. Generally the hardware illustrated in FIG. 3 can be divided into two subsets including single event processing circuitry and the coincidence detection circuitry 200. The single event processing circuitry, as the label implies, processes data corresponding to a single EDP and generates three types of data related thereto including a unit identifier Id, a crystal identifier Ci and a time stamp Ts for each detected even within the energy level range associated with an absorbed photon. To this end, the single event processing circuitry includes identifier 220, clock 58, converter 56, circuit 68 and module 222. The coincidence circuitry 200, as its label implies, identifies coincidence EDP pairs.

Construction and operation of many of the components identified in FIG. 3 are well known within the PET industry and therefore will not be explained here in detail. To this end, signals from each of PMTs 22 in FIG. 2 are received via lines 26 by energy and crystal identifier 220 which uses the received signals to perform two separate functions. First, for events that are not discarded, identifier 220 uses the signals form the four PMTs to determine which of the crystals (e.g., see 180, 182 in FIG. 2) was impacted by the received photon. The corresponding crystal is identified by a signal $C_i$. Second, identifier 220 integrates the received energy from all four PMTs in the detector unit and then determines if integrated energy is within the energy range which is known to be caused by a detected photon. Identifier 220 discards any detected events if the integrated energy of a scintillation is outside the range of 511 keV +/−20%. The crystal identification signal $C_i$ for events with integrated energy inside the range of 511 keV ±20% is provided to coincidence detection circuitry 200. For a better understanding of how identifier 220 operates refer to U.S. Pat. No. 6,232,604 which issued on May 15, 2001, and is entitled "Analog Time Adjustment For Coincidence Detection Electronics", and which is incorporated in its entirety herein by reference.

TPC 68 also receives the signals on lines 26 and sums the received signals thereby generating a total energy signal for the detector unit 20. Circuit 68 then compares the summed energy signal to a threshold. The threshold energy level is typically 100 keV. When the total energy signal exceeds the threshold energy level, circuit 68 generates an event detection pulse (EDP) Q which is provided to the TDC 56 and the control logic module 222.

In addition to receiving pulse Q, TDC 56 also receives a master clock signal from clock 58. The clock signal is a periodic reference signal that is typically in the hundreds of nanoseconds. As indicated above, for the purposes of this explanation it has been assumed that the master clock signal occurs every 250 nanoseconds (i.e., each master clock cycle is 250 nanoseconds). The TDC 56 further divides each clock cycle into time stamps separated by identical time periods. For the purposes of this explanation it will be assumed that TDC 56 divides each 250 nanosecond clock cycle into 192 separate periods, each period identifiable by a separate and unique time stamp.

Thus, TDC 56 generates a time stamp Ts corresponding to each EDP Q and referenced from the most recent master clock signal and provides the time stamp Ts to coincidence detection circuitry 200. Time stamp Ts indicates, within a matter of nanoseconds, the precise time when a scintillation event occurred.

Module 222 receives the output of each circuit 68 (i.e. a separate circuit 68 for each detector unit in a module for a total of six outputs) and generates a detector unit identification signal Id indicating the detector unit which detected the scintillation event and generated the EDP Q. Unit identification signal Id is provided to coincidence detection circuitry 200. Although not illustrated TPC 68 or additional hardware is typically provided to delay each EDP Q a specific delay period to compensate for known system processing delays. Thus, for instance, in some cases each EDP Q will be delayed for tens of nanoseconds (e.g., 64 nsec.) so that a delayed signal Q is provided to converter 56 and module 222. For a better understanding of construction and operation of each of the integrator and TPC 68, and the control logic module 222 and one EDP delay method, refer to U.S. Pat. No. 6,232,604 which is incorporated herein by reference.

Coincidence detection circuitry 200 accepts the detector and crystal identifying signals Id and Ci and the associated time stamp Ts as an event data packet and determines if any two events are in coincidence. Coincidence is determined by a number of factors. First, the time stamps Ts in each event data packet must be within a small time window W/2 of each other. Second, the locations indicated by the two event data packets must lie on a straight line which passes through the FOV in imaging area 12 (see FIG. 1). Events which cannot be paired as coincidence events are discarded. Coincidence event pairs are provided to sorter 34 as coincidence data packets which are in turn stored in memory 43 (see FIG. 1).

Figure 4:
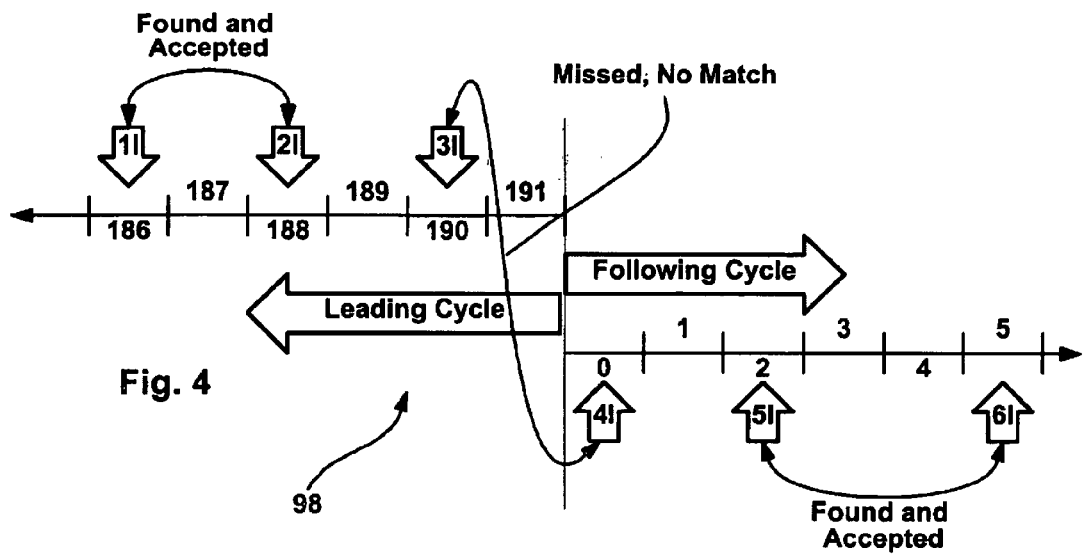
FIG. 4 is a timing diagram illustrating consecutive leading and following master clock cycles and corresponding exemplary event detection pulses (EDPs) that have been associated with specific time stamps.
Figure 5:
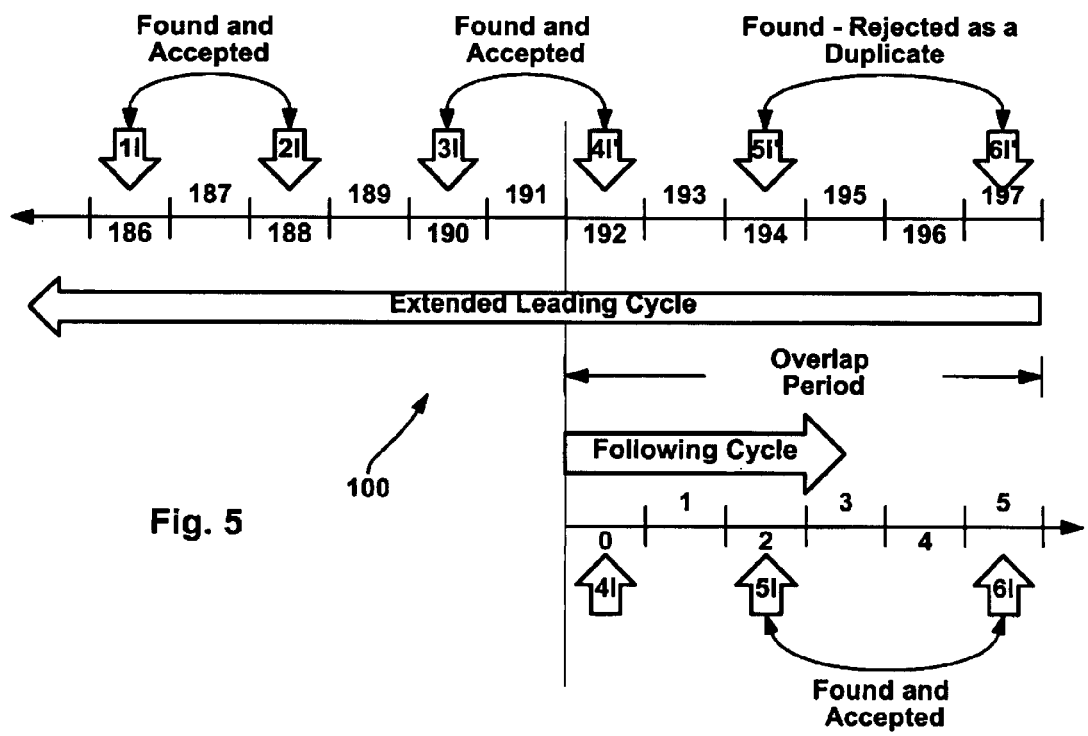
FIG. 5 is a similar to FIG. 4, albeit illustrating an extended leading cycle where EDPs from the beginning of the following cycle have been copied into the extended portion of the leading cycle.

Referring still to FIG. 3, while circuitry 200 may include many additional components, for the purposes of this explanation, coincidence detection circuitry 200 includes a cycle extender 61, a time stamp duplicator 63, comparison circuitry 67 and a duplicate eliminator 69. Referring also to FIG. 5, a timing diagram 100 similar to diagram 98 in FIG. 4 illustrates operation of the coincidence detection components in accordance with the present invention and includes time stamps 186 through 197 that correspond to an extended first clock cycle and stamps 1 through 5 that correspond to a second clock cycle. Diagram 100 is different than diagram in 98 in several ways. First, consistent with the present invention, the diagram 100 includes an overlap period having a duration of W/2 (i.e., six times the time stamp period) that has been tacked onto the leading cycle. This extending process is facilitated by cycle extender 61. The resulting leading cycle is identified in FIG. 5 as an "extended leading cycle" with the overlap period, as the label implies, overlapping the following cycle by W/2.

Second, each of the time stamps corresponding to EDPs 4l, 5l and 6l in the following cycle that occur during the overlap period have been copied or duplicated in the overlap period. To this end, EDP 4l having a time stamp of 0 in the following cycle has been copied to time stamp 192 as EDP 4l' in the extended cycle, EDP 5l having a time stamp of 2 in the following cycle has been copied to time stamp 194 as EDP 5l' in the extended leading, EDP 6l having a time stamp of 5 in the following cycle has been copied to time stamp 197 as EDP 6l' in the extended leading cycle. This duplicating process is accomplished by duplicator 63.

After the EDP time stamps from the following cycle that occurs during the overlap period have been copied to the overlap period, comparison circuitry 67 compares all of the EDP time stamps in the extended leading cycle to identify coincidence pairs. Thus, in the present example, because each of EDPs 1l, 2l, 3l, 4l', 5l' and 6l' have time stamps that are in the extended leading cycle, each possible coincidence pair including time stamps corresponding to EDPs 1l and 2l, 2l and 3l, 3l and 4l', 4l' and 5l', 5l' and 6l', 1l and 3l, 1l and 4l', 2l and 4l', 2l, and 5l', 3l and 4l', 3l and 5' and 4l' and 6l' are considered for coincidence pairing. In the present case, as in the case of FIG. 4, the pair including EDPs 11 and 21 and the pair including EDPs 51' and 61' are identified during extended period comparison. In addition, the pair including EDPs 31 and 41' is also identified. The identified coincidence pairs are provided to duplicate eliminator 69.

After all of the coincidence pairs in the extended leading period have been identified, assembly 11 performs the same process with the following clock cycle as a new leading clock cycle and the clock cycle that comes after the following clock cycle as a new following clock cycle. Thus, referring again to FIG. 5, comparison circuitry 67 processes each of the EOPs having time stamps in the overlap period (i.e., following cycle EDPs having time stamps that occur during the extension period) a second time. In the present case this means that assembly 11 would process EDPs 41, 51 and 61 despite the fact that copies 41', 51' and 61' have already been processed once. Such dual processing would result in double counting of the coincidence pair including EDPs 51 and 61 and thus would cause a data acquisition error.

In order to avoid double counting of coincidence pairs, whenever both EDPs in a coincidence pair have time stamps that fall within a single "normal" period and also within an extension or overlap period, the pair is not counted and instead is simply discarded. Here the phrase "normal period" is used to refer to an unmodified (i.e., original non-extended) clock cycle. Because these pairs are counted during coincidence pair processing in a temporally adjacent clock cycle (i.e., the next clock cycle in the previously described embodiment), the pair is accounted for. To this end, duplicate eliminator 69 determines when both EDPs in a coincidence pair occur during an overlap period and eliminates the pair (i.e., fails to increment a counter corresponding to the coincidence pair). Eliminator 69 outputs surviving coincidence pairs to sorter 34 for sorting and storage as indicated above.

Figure 6:
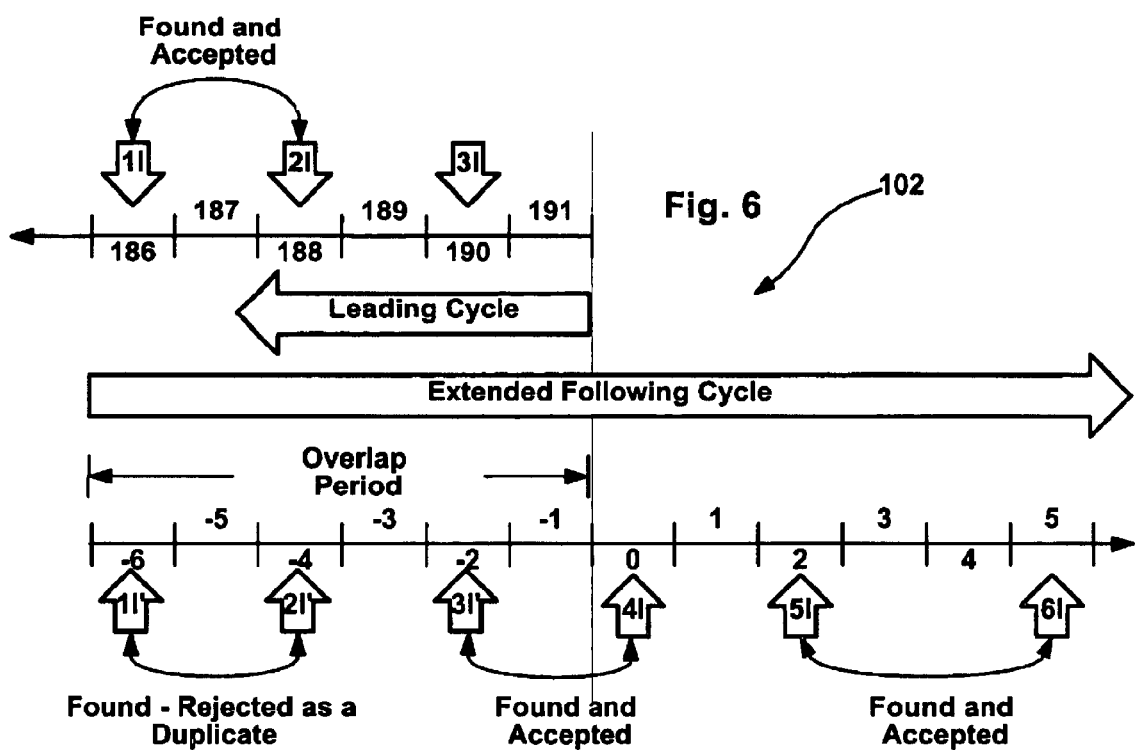
FIG. 6 is a is similar to FIG. 5 albeit illustrating an extended following cycle with EDPs from the leading cycle copied into the extended portion of the following cycle.

While the invention has been described above as one wherein clock cycles are extended by adding an extension period to the ends of the cycles, the present invention also contemplates embodiments where clock cycles are extended by adding an extension period to the beginning of each clock cycle. To this end, referring to FIG. 6, a diagram 102 illustrates the end of a leading and the beginning of a following clock cycle in a fashion similar to that in FIG. 5. In FIG. 6, however, an overlap period W/2 (i.e., again, the duration defined by 6 time stamps including stamps −6, −5, −4, −3, −2 and −1) is added to the beginning of the following period instead of at the end of the leading period. In this case the time stamps corresponding to the EDPs in the overlap period (i.e., leading cycle EDPs having time stamps that occur during the overlap period) are copied to the extended following cycle and more specifically to the overlap period. Thus, EDP 11 having a time stamp of 186 in the leading cycle has been copied to time stamp −6 as EDP 11' in the extended following cycle, EDP 21 having a time stamp of 188 in the leading cycle has been copied to time stamp −4 as EDP 21' in the extended following cycle and EDP 31 having a time stamp of 190 in the leading cycle has been copied to time stamp −2 as EDP 31' in the extended following cycle. Referring also to FIG. 3, the extending and copying processes are carried out by extender and duplicator 61 and 63, respectively in a manner similar to that described above.

Once again, after EDP time stamps have been duplicated, comparison circuitry 67 and duplicate eliminator 69 operate to identify coincidence pairs and then eliminate the possibility of counting a coincidence pair more than once. Surviving coincidence pairs are provided to sorter 34.

Referring now to FIG. 7, a flow chart of an exemplary inventive method 150 is illustrated. Referring also to FIG. 3, beginning at block 152, for consecutive leading and following clock cycles where each of the leading and following cycles are master cycles, extender 61 identifies an overlap period (i.e., W/2) that includes a portion of a first of the master cycles adjacent a second of the master cycles. Here the first master cycle may be either the leading or the following cycle depending on which method, the method of FIG. 5 or the method of FIG. 6, is used to account for pairs that include a separate EDP in each of the first and second cycles. Where the first master cycle is the leading cycle the overlap period is the ending of the leading period and where the first cycle is the following cycle the overlap period is the beginning of the following period.

At block 154, after the overlap period is identified, extender 61 adds the overlap period to the second of the master cycles to generate an extended cycle. Thus, where the second cycle is the following cycle, the overlap period is added to the beginning of the following period to generate an extended period and where the second cycle is the leading cycle, the overlap period is added to the ending of the leading period to generate the extended period.

Continuing, at block 156, duplicator 63 identifies overlap events that occur during the overlap period in the first of the master cycles. For example, referring again to FIG. 5, where the following cycle is the first cycle, duplicator 63 identifies EDPs 41, 51 and 61 which each occur during the overlap period. Next, at block 158, duplicator 63 copies EDP time stamps (e.g., the EDPs) to the overlap period. Thus, as in FIG. 5, EDP stamps 41, 51 and 61 are copied as stamps 41', 51' and 61'.

At block 160 comparison circuitry 67 compares the events in the extended cycle to identify coincidence pairs which are provided to eliminator 69. At decision block 162, for each coincidence event pair, eliminator 69 determines if both events in the pair occur during the overlap period. Where both events in a pair do not occur during the overlap period, control passes to block 164 where eliminator 69 passes the event pair onto sorter 34 to be counted and stored after which control passes to block 166. Where both events in a pair do occur during the overlap period, control is routed around block 164 to block 166 so that the coincidence pair is not counted.

At block 166 the process above is repeated with the following cycle as the leading cycle and the cycle after the following cycle as the following cycle. This process continues for each clock cycle as a rolling operation.

It should be recognized by those skilled in the art that the process of moving EDPs form one master clock cycle to another is academic and is done routinely already when EDP Q signals are delayed to compensate for processing delays. In fact, because processing delays and corresponding compensation typically are on the order of tens of nanoseconds (e.g. 64 nsec.) and delays of this magnitude are approximately one quarter of a typical clock cycle (e.g., 250 nsec.), often as many as one fourth of all EDPs are already moved from one cycle to the next. Thus, copying of EDPs and time stamps among cycles is a simple matter of system programming.

It should be understood that the methods and apparatuses described above are only exemplary and do not limit the scope of the invention, and that various modifications could be made by those skilled in the art that would fall under the scope of the invention.

To apprise the public of the scope of this invention, the following claims are made:

What is claimed is:

1. A method for reducing event loss in a digital time stamped PET scanner including a master clock that has a master clock cycle and an event processing circuit that divides each clock cycle into a plurality of time stamps, the scanner also including coincidence detection circuitry that compares time stamps within each clock cycle to identify coincidence event pairs, the method comprising the steps of:
   a. for consecutive leading and following clock cycles where each of the leading and following cycles are master cycles, identifying an overlap period that includes a portion of a first of the master cycles adjacent a second of the master cycles;
   b. adding the overlap period to the second of the master cycles to generate an extended cycle;
   c. identifying overlap events that occur during the overlap period in the first of the master cycles;
   d. copying the overlap events to the overlap period in the extended cycle; and
   e. comparing events in the extended cycle to identify coincidence event pairs.

2. The method of claim 1 wherein the scanner is used to collect events during a plurality of consecutive clock cycles and wherein the method further includes the step of repeating steps (a) through (e) for each two consecutive clock cycles.

3. The method of claim 1 further including the step of counting event pairs and wherein the step of comparing includes, for each coincidence event pair, determining if both events in the pair occur during the overlap period and, where both events occur during the overlap period, skipping the step of counting the event pair.

4. The method of claim 1 wherein the leading cycle and following cycle are the first and second cycles, respectively, so that the step of identifying an overlap period includes the step of identifying the ending portion of the leading cycle adjacent the following cycle.

5. The method of claim 1 wherein the leading cycle and following cycle are the second and first cycles, respectively, so that the step of identifying an overlap period includes the step of identifying the beginning portion of the following cycle adjacent the leading cycle.

6. The method of claim 1 wherein the scanner is characterized by a coincidence window and the overlap period has a duration at least as long as one half the coincidence window.

7. An apparatus for reducing event loss in a digital time stamped PET scanner including a master clock that has a master clock cycle and an event processing circuit that divides each clock cycle into a plurality of time stamps, the scanner also including coincidence detection circuitry that compares time stamps within each clock cycle to identify coincidence event pairs, the apparatus comprising:

an extender that for consecutive leading and following clock cycles where each of the leading and following cycles are master cycles, identifies an overlap period that includes a portion of a first of the master cycles adjacent a second of the master cycles and adds the overlap period to the second of the master cycles to generate an extended cycle;

a duplicator for identifying overlap events that occur during the overlap period in the first of the master cycles and copying the overlap events to the overlap period in the extended cycle;

a comparator for comparing events in the extended cycle to identify coincidence event pairs; and a sorter for counting the event pairs.

8. The apparatus of claim 7 wherein the scanner is used to collect events during a plurality of consecutive clock cycles and wherein the apparatus repeats the extending, copying, comparing and counting process for each two consecutive clock cycles.

9. The apparatus of claim 7 further including a duplicate eliminator wherein that, for each coincidence event pair, determines if both events in the pair occur during the overlap period and, where both events occur during the overlap period, causes the sorter to skip counting the event pair.

10. The apparatus of claim 7 wherein the leading cycle and following cycle are the first and second cycles, respectively, so that the extender identifies an overlap period by identifying the ending portion of the leading cycle adjacent the following cycle.

11. The apparatus of claim 7 wherein the leading cycle and following cycle are the second and first cycles, respectively, so that the extender identifies an overlap period by identifying the beginning portion of the following cycle adjacent the leading cycle.

12. The apparatus of claim 7 wherein the scanner is characterized by a coincidence window and the overlap period has a duration at least as long as one half the coincidence window.

13. A method for reducing event loss in a digital time stamped PET scanner including a master clock that has a master clock cycle and an event processing circuit that divides each clock cycle into a plurality of time stamps, the scanner also including coincidence detection circuitry that compares time stamps within each clock cycle to identify coincidence event pairs, the method comprising the steps of:
   a. for consecutive leading and following clock cycles where each of the leading and following cycles are master cycles, identifying an overlap period that includes a portion of a first of the master cycles adjacent a second of the master cycles;
   b. adding the overlap period to the second of the master cycles to generate an extended cycle;
   c. identifying overlap events that occur during the overlap period in the first of the master cycles;
   d. copying the overlap events to the overlap period in the extended cycle;
   e. comparing events in the extended cycle to identify coincidence event pairs;
   f. for each coincidence event pair, determining if both events in the pair occur during the overlap period and, where both events occur during the overlap period, skipping to step (h);
   g. counting the event pairs; and
   h. repeating steps (a) through (g) with the following cycle as a new leading cycle and the cycle after the following cycle as a new following cycle.

14. The method of claim 13 wherein the leading cycle and following cycle are the first and second cycles, respectively, so that the step of identifying an overlap period includes the step of identifying the ending portion of the leading cycle adjacent the following cycle.

15. The method of claim 13 wherein the leading cycle and following cycle are the second and first cycles, respectively, so that the step of identifying an overlap period includes the step of identifying the beginning portion of the following cycle adjacent the leading cycle.

16. The method of claim 15 wherein the scanner is characterized by a coincidence window and the overlap period has a duration at least as long as one half the coincidence window.

17. An apparatus for reducing event loss in a digital time stamped PET scanner including a master clock that has a master clock cycle and an event processing circuit that divides each clock cycle into a plurality of time stamps, the scanner also including coincidence detection circuitry that compares time stamps within each clock cycle to identify coincidence event pairs, the apparatus comprising:

a. for consecutive leading and following clock cycles where each of the leading and following cycles are master cycles, means for identifying an overlap period that includes a portion of a first of the master cycles adjacent a second of the master cycles;

b. means for adding the overlap period to the second of the master cycles to generate an extended cycle;

c. means for identifying overlap events that occur during the overlap period in the first of the master cycles;

d. means for copying the overlap events to the overlap period in the extended cycle;

e. means for comparing events in the extended cycle to identify coincidence event pairs; and f. means for counting the event pairs.

18. The apparatus of claim 17 wherein the means for comparing includes, for each coincidence event pair, means for determining if both events in the pair occur during the overlap period and, where both events occur during the overlap period, means for skipping the step of counting the event pair.

19. The apparatus of claim 17 wherein the leading cycle and following cycle are the first and second cycles, respectively, so that the means for identifying an overlap period includes a means for identifying the ending portion of the leading cycle adjacent the following cycle.

20. The method of claim 17 wherein the leading cycle and following cycle are the second and first cycles, respectively, so that the means for identifying an overlap period includes a means for identifying the beginning portion of the following cycle adjacent the leading cycle.

* * * * *